US010491065B2

(12) United States Patent
Sasaki et al.

(10) Patent No.: US 10,491,065 B2
(45) Date of Patent: Nov. 26, 2019

(54) PERMANENT MAGNET SYNCHRONOUS MOTOR

(71) Applicants: Nissan Motor Co., Ltd., Yokohama-shi, Kanagawa (JP); Wisconsin Alumni Research Foundation, Madison, WI (US)

(72) Inventors: Kensuke Sasaki, Madison, WI (US); Takashi Fukushige, Kanagawa (JP); Takashi Kato, Kanagawa (JP); Robert D. Lorenz, Madison, WI (US); Apoorva Athavale, Madison, WI (US)

(73) Assignees: Nissan Motor Co., Ltd., Yokohama (JP); Wisconsin Alumni Research Foundation, Madison, WI (US)

( * ) Notice: Subject to any disclaimer, the term of this patent is extended or adjusted under 35 U.S.C. 154(b) by 396 days.

(21) Appl. No.: 15/509,219

(22) PCT Filed: Sep. 11, 2014

(86) PCT No.: PCT/US2014/055049
§ 371 (c)(1),
(2) Date: Mar. 7, 2017

(87) PCT Pub. No.: WO2016/039746
PCT Pub. Date: Mar. 17, 2016

(65) Prior Publication Data
US 2017/0279322 A1    Sep. 28, 2017

(51) Int. Cl.
*H02K 1/27*    (2006.01)
*H02K 21/14*    (2006.01)
(Continued)

(52) U.S. Cl.
CPC ........... *H02K 1/2766* (2013.01); *G01N 27/82* (2013.01); *H02K 1/27* (2013.01); *H02K 1/276* (2013.01);
(Continued)

(58) Field of Classification Search
CPC ........ H02K 1/27; H02K 1/276; H02K 1/2766; H02K 21/14; H02K 21/12; H02K 2213/03
(Continued)

(56) References Cited

U.S. PATENT DOCUMENTS

| 2,632,123 A * | 3/1953 | Kober .................... H02K 21/14 310/156.77 |
| 2010/0194228 A1* | 8/2010 | Lee ........................ H02K 29/03 310/156.53 |

(Continued)

FOREIGN PATENT DOCUMENTS

| CN | 103986259 A | 8/2014 |
| JP | 2006-280195 A | 10/2006 |

(Continued)

*Primary Examiner* — Mang Tin Bik Lian
*Assistant Examiner* — Alexander Moraza
(74) *Attorney, Agent, or Firm* — Global IP Counselors, LLP

(57) ABSTRACT

A permanent magnet synchronous motor includes a stator with a stator winding, a rotor with a rotor core rotatable relative to the stator, and a magnetic structure with at least one permanent magnet mounted to the rotor core. The magnetic structure produces a magnetic flux that flows between different magnetic poles of the magnetic structure through a main magnetic flux path that passes through the stator winding of the stator via an air gap and a leakage magnetic flux path that is located within the rotor core about an end portion of the permanent magnet near the air gap. The stator, the rotor and the magnetic structure being further configured to satisfy predetermined relationships in regards (Continued)

to the magnetic resistance of the main magnetic flux path and the leakage magnetic flux path, the magnetomotive force of the magnets and the stator.

9 Claims, 4 Drawing Sheets

(51) Int. Cl.
*H02K 21/12* (2006.01)
*G01N 27/82* (2006.01)
*H02K 21/02* (2006.01)

(52) U.S. Cl.
CPC .............. *H02K 21/02* (2013.01); *H02K 21/12* (2013.01); *H02K 21/14* (2013.01); *H02K 2213/03* (2013.01)

(58) Field of Classification Search
USPC ............ 310/156.53, 156.56, 156.57, 156.83, 310/216.094, 216.106, 216.077, 156.49
See application file for complete search history.

(56) References Cited

U.S. PATENT DOCUMENTS

| 2013/0119812 A1* | 5/2013 | Takizawa | H02K 1/276 310/156.53 |
| 2014/0217849 A1 | 8/2014 | Soma et al. | |
| 2015/0280502 A1* | 10/2015 | Hirotani | H02K 29/03 310/68 R |
| 2016/0301268 A1* | 10/2016 | Watanabe | H02K 9/19 |

FOREIGN PATENT DOCUMENTS

| JP | WO2014/027631 A1 | 7/2016 |
| WO | 2014/027631 A1 | 2/2014 |

* cited by examiner

PERMANENT MAGNET SYNCHRONOUS MOTOR

CROSS-REFERENCE TO RELATED APPLICATION

This application is a U.S. National stage of International Application No. PCT/JP2014/055049, filed Sep. 11, 2014, the entire contents of International Application No. PCT/JP2014/055049 are hereby incorporated herein by reference.

BACKGROUND

Field of the Invention

The present invention generally relates to a permanent magnet synchronous motor. More specifically, the present invention relates to a permanent magnet synchronous motor with a rotor having a permanent magnet.

Background Information

Electric vehicles and hybrid electric vehicles (HEV) include an electric motor that operates as a drive source for the vehicle. In a purely electric vehicle, the electric motor operates as the sole drive source. On the other hand, an HEV includes an electric motor and a conventional combustion engine that operate as the drive sources for the vehicle based on conditions as understood in the art.

An electric motor which includes a rotor with a low-coercive-force magnet to achieve variable magnetization characteristics (which is called variable magnetization motor hereinafter) is known (see Japanese Unexamined Patent Application Publication No. 2006-280195, for example). For example, as shown in FIG. 4, the variable magnetization motor has a rotor 101 having a rotor core 102, a plurality of low-coercive-force magnets 103, and a plurality of high-coercive-force magnets 104. With this configuration, the magnetization level of the low-coercive-force magnets 103 can be changed by a magnetic field generated by a current in a stator winding of a stator. Specifically, the magnetization level of the low-coercive-force magnets 103 can be changed by d-axis flux according to the operational state of the motor to improve the efficiency of the motor. In particular, the magnetization level can be increased to increase the torque generated by the motor.

SUMMARY

However, with the variable magnetization motor, in order to change the magnetization level of the motor, an instantaneous increase in load current applied to the stator winding is required, which increases the copper loss in the motor. Thus, although efficiency of variable magnetization motor is improved compared to conventional machines, the additional copper losses that occur during the change of magnetization state limits the amount of improvement.

Accordingly, it is desirable to provide an improved motor with an improved efficiency by reducing the copper loss accompanied by changing the magnetization level of the variable magnetization motor.

In view of the state of the known technology, one aspect of a permanent magnet synchronous motor includes a stator with a stator winding, a rotor with a rotor core rotatable relative to the stator, and a magnetic structure with at least one permanent magnet mounted to the rotor core. The rotor being radially inwardly or outwardly disposed relative to the stator with an air gap therebetween. The magnetic structure produces a magnetic flux that flows between different magnetic poles of the magnetic structure through a main magnetic flux path that passes through the stator winding of the stator via the air gap and a leakage magnetic flux path that is located within the rotor core about an end portion of the permanent magnet near the air gap. The stator, the rotor and the magnetic structure being further configured to satisfy the following expressions:

$$Vs \geq \frac{Rg + Rs}{Rr} Vm$$

$$\eta = \frac{Rg + Rs}{Rb + Rg + Rs} \geq 0.2$$

where Vs represents magnetomotive force of the stator winding, Vm represents magnetomotive force of the magnetic structure, Rg represents magnetic resistance of the air gap, Rs represents magnetic resistance of the stator along the main magnetic flux path, Rr represents magnetic resistance of the rotor core along the main magnetic flux path, Rb represents magnetic resistance of the rotor core along the leakage magnetic flux path, and η represents a ratio of a leakage magnetic flux of the magnetic flux that flows through the leakage magnetic flux path relative to a total magnetic flux of the magnetic flux that is produced by the magnetic structure.

BRIEF DESCRIPTION OF THE DRAWINGS

Referring now to the attached drawings which form a part of this original disclosure.

DETAILED DESCRIPTION OF EMBODIMENTS

Selected embodiments will now be explained with reference to the drawings. It will be apparent to those skilled in the art from this disclosure that the following descriptions of the embodiments are provided for illustration only and not for the purpose of limiting the invention as defined by the appended claims and their equivalents.

First Embodiment

Figure 1:
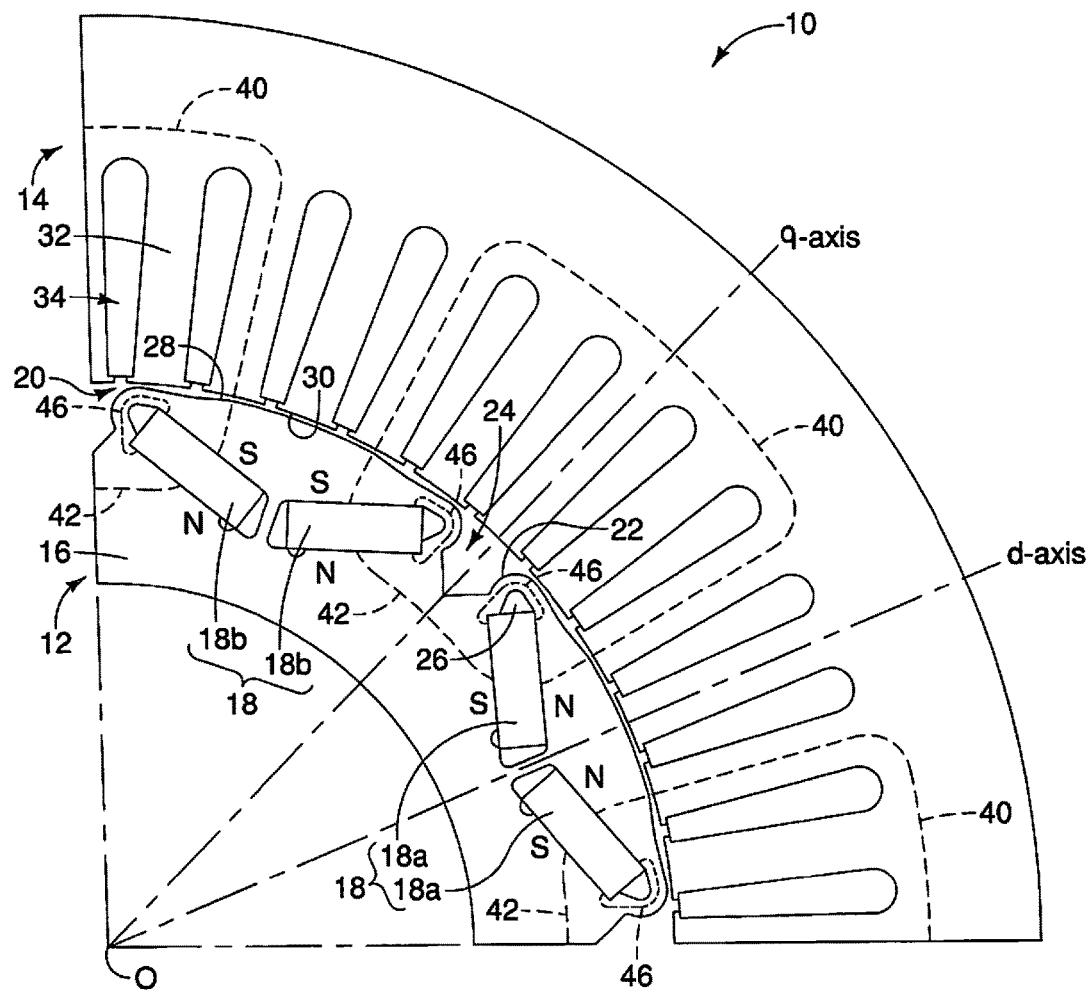
FIG. 1 is a partial cross-sectional schematic view of a permanent magnet synchronous motor in accordance with to a first embodiment.

Referring to FIG. 1, a permanent magnet synchronous motor 10, which can also be referred to as an interior permanent magnet motor, is illustrated in accordance with to a first embodiment. As shown in FIG. 1, the motor 10 basically includes a rotor 12 and a stator 14. The motor 10 can be employed in any type of electric vehicle or HEV such as an automobile, truck, SUV and so on, and in any other type of apparatus as understood in the art. The rotor 12 and the stator 14 can be made of metal or any other suitable material as understood in the art.

In the illustrated embodiment, the rotor 12 has a rotor core 16. The motor 10 also includes a plurality of magnets 18 that is fixedly mounted to the rotor core 16. The rotor core 16 is rotatable relative to the stator 14 about a center rotational axis O of the motor 10, and is radially inwardly disposed relative to the stator 14 with an air gap 20 therebetween. The rotor core 16 is configured to include a plurality pairs of leakage sections 22, a plurality of flux barriers 24 and a plurality pairs of side openings 26. The rotor core 16 is basically formed as a one-piece, unitary member. The configurations of the rotor core 16 will be further described in detail below. In the illustrated embodiment, the rotor core 16 is radially inwardly disposed relative to the stator 14 with the air gap 20 therebetween. However, the the rotor core 16 can be radially outwardly disposed relative to the stator 14 with an air gap therebetween as understood in the art.

In the illustrated embodiment, the stator 14 is concentrically arranged relative to the rotor 12 with respect to the center rotational axis O of the motor 10. As mentioned above, the stator 14 is radially outwardly disposed relative to the rotor 12 with the air gap 20 therebetween. In particular, as illustrated in FIG. 1, the air gap 20 is present between an outer circumference 28 of the rotor 12 and an inner circumference 30 of the stator 14 to enable the rotor 12 to rotate unrestrictedly or substantially unrestrictedly about the center rotational axis O. The stator 14 basically includes a plurality of stator teeth 32, a plurality of stator windings 34, and other components which can be configured in any conventional manner. In the illustrated embodiment, the stator teeth 32 are configured as wide stator teeth as known in the art. However, the stator teeth 32 can have any suitable size, and the stator 14 can include any number of stator teeth 32 to achieve the operability of the embodiments discussed herein. In this example, the stator teeth 32 are open to the inner circumference 30 of the stator 14, but can be closed if desired. The stator windings 34 are made of copper or aluminum wires wound about the stator teeth 32. However, the stator windings 34 can be made of any suitable type of material as known in the art. In the illustrated embodiment, the stator 14 can be employ a conventional stator as known in the art. Thus, detailed descriptions will be omitted for the sake of brevity.

In the illustrated embodiment, the magnets 18 are spaced between adjacent pairs of the flux barriers 24 about the circumference of the rotor 12. As shown in FIG. 1, each of the magnets 18 has a pair of permanent magnet pieces 18a or 18b (e.g., at least one permanent magnet) to define each of the motor poles of the motor 10 with alternate polarities. In the illustrated embodiment, four pairs of the magnet pieces 18a and four pairs of the magnet pieces 18b are alternately arranged in the circumferential direction about the center rotational axis O to define eight motor poles of the motor 10. Specifically, in the illustrated embodiment, the north poles of the magnet pieces 18a are radially outwardly arranged relative to the south poles of the magnet pieces 18a, while the south poles of the magnet pieces 18b are radially outwardly arranged relative to the north poles of the magnet pieces 18b, for example. Thus, in the illustrated embodiment, the rotor 12 includes eight pairs of the magnet pieces 18a and 18b which are positioned between eight flux barriers 24 and spaced at 45 degree intervals in the circumferential direction about the center rotational axis O. However, the number of the magnet pieces 18a and 18b or the number of the magnets 18 can change with respect to a change in the number of flux barriers 24. Furthermore, each magnet 18 can be configured as a single magnet piece or more than two magnet pieces. As shown in FIG. 1, a d-axis passes through a center of each magnet 18. In other words, the d-axis passes through between the pair of magnet pieces 18a or 18b. On the other hand, a q-axis passes through each flux barriers 24. In other words, the q-axis passes between adjacent pair of magnets 18, or adjacent pair of the magnet pieces 18a and 18b. However, the magnets 18 or the flux barriers 24 can be positioned at any suitable location with respect to the d-axis and the q-axis to achieve the operability of the embodiments discussed herein. In the illustrated embodiment, the pair of the magnet pieces 18a extends radially and inwardly as circumferentially moving towards each other. Similarly, the pair of the magnet pieces 18b extends radially and inwardly as circumferentially moving towards each other. However, the magnet pieces 18a and 18b can be arranged in a different manner as needed and/or desired.

In the illustrated embodiment, the magnets 18 form a magnetic structure that produces magnetic flux that flows between different magnetic poles of the magnets 18 through a plurality of first main magnetic flux paths 40, a plurality of second main magnetic flux paths 42, and a plurality of leakage magnetic flux paths 46. In the illustrated embodiment, as shown in FIG. 1, each of the first main magnetic flux paths 40 extends from one magnetic pole of one of the magnets 18 (e.g., the north pole of the magnet piece 18a) to the other magnetic pole of adjacent one of the magnets 18 (e.g., the south pole of the magnet piece 18b), and passes through the stator winding 34 of the stator 14 via the air gap 20, while each of the second main magnetic flux paths 42 extends from the one magnetic pole of the adjacent one of the magnets 18 (e.g., the north pole of the magnet piece 18b) to the other magnetic pole of the one of the magnets 18 (e.g., the south pole of the magnet piece 18a), and passes through the rotor core 16. In the illustrated embodiment, a pair of the first and second main magnetic flux paths 40 and 42 forms a main magnetic flux path that passes through the stator winding 34 of the stator 14 via the air gap 20. On the other hand, each of the leakage magnetic flux paths 46 is located within the rotor core 16 about an end portion of respective one of the magnet pieces 18a and 18b near the air gap 20. In the illustrated embodiment, each of the leakage magnetic flux paths 46 extends between different magnetic poles of respective one of the magnet pieces 18a and 18b (e.g., between north pole and south pole of the magnet piece 18a or 18b) through respective one of the leakage sections 22 of the rotor core 16.

As mentioned above, the rotor core 16 has the leakage sections 22, the flux barriers 24 and the side openings 26. Although only two pairs of the leakage sections 22 and only two pairs of the side openings 26 for two magnets 18 or two motor poles of the motor 10 are shown in FIG. 1, the rotor core 16 has eight pairs of the leakage sections 22 and eight pairs of the side openings 26 corresponding to eight magnets 18 or eight motor poles of the motor 10 in total. Similarly, Although only one full and two partial flux barriers 24 for two magnets 18 or two motor poles of the motor 10 are shown in FIG. 1, the rotor core 16 has eight flux barriers 24 between adjacent pairs of eight magnets 18 or eight motor poles of the motor 10 in total. However, the rotor core 16 can include as many numbers of the leakage sections 22, the flux barriers 24 and the side openings 26 as deemed appropriate for the environment in which the motor 10 is employed. In the illustrated embodiment, the rotor core 16 is configured in a mirror symmetric manner with respect to the d-axis and the q-axis.

As shown in FIG. 1, the leakage sections 22 basically include a U-shaped part that extends between different magnetic poles of the magnets 18 to define the leakage magnetic flux paths 46 therewithin, respectively. In other words, in the illustrated embodiment, the leakage magnetic flux paths 46 extend through the leakage sections 22, respectively. As shown in FIG. 1, the leakage sections 22 for adjacent pairs of the magnets 18 circumferentially face with each other via the flux barriers 24, respectively. In other words, the flux barriers 24 are disposed between adjacent pairs of the leakage sections 22. Specifically, the flux barriers 24 are disposed between the adjacent pairs of the magnets 18 or the adjacent pairs of the motor poles of the motor 10 (e.g., between the magnet piece 18a and the magnet piece 18b that is adjacent to the magnet piece 18a). In the illustrated embodiment, the flux barriers 24 are configured as air gaps between the adjacent pairs of the leakage sections 22. Thus, the magnetic resistance calculated based on a magnetic path width and a magnetic path length of the leakage magnetic flux path 46 on the leakage section 22 is smaller than the magnetic resistance of a magnetic path extending between different magnetic poles of the adjacent pair of the magnets 18 (e.g., between the north pole of the magnet piece 18a and the south pole of the magnet piece 18b that is adjacent to the magnet piece 18a) through the flux barriers 24. In the illustrated embodiment, the flux barriers 24 are radially outwardly open to face with the inner circumference 30 of the stator 14, and radially extend from the outer circumference 28 of the rotor 12 to a position radially inward relative to a radially inward boundary of the side openings 26. In the illustrated embodiment, the flux barriers 24 are configured as air gaps. However, the flux barriers 24 can also include any suitable type of insulating material as is conventional in the art. The side openings 26 are circumferentially adjacent to the end portions of the magnet pieces 18a and 18b such that the leakage sections 22 are disposed between the flux barriers 24 and the side openings 26, respectively. Thus, the leakage magnetic flux paths 46 that extend through the leakage sections 22 extend on the rotor core 16 between the flux barriers 24 and the side openings 26, respectively.

In the illustrated embodiment, the rotor 12, the stator 14, and the magnets 18 (e.g., the magnetic structure) are further configured to satisfy the following expressions (1) and (2) for one motor pole of the motor 10.

$$Vs \geq \frac{Rg + Rs}{Rr} Vm \quad (1)$$

$$\eta = \frac{Rg + Rs}{Rb + Rg + Rs} \geq 0.2 \quad (2)$$

Here, Vs represents the magnetomotive force of the stator windings 34 for one motor pole of the motor 10, and Vm represents the magnetomotive force of the magnet 18 for one motor pole of the motor 10. Rg represents the magnetic resistance of the air gap 20 for one motor pole of the motor 10, Rs represents the magnetic resistance of the stator 14 along the first main magnetic flux path 40 for one motor pole of the motor 10, Rr represents the magnetic resistance of the rotor core 16 along the second main magnetic flux path 42 for one motor pole of the motor 10, Rb represents the magnetic resistance of the rotor core 16 along the leakage magnetic flux path 46, and η represents a ratio of a leakage magnetic flux of the magnetic flux that flows through the leakage magnetic flux path 46 relative to a total magnetic flux of the magnetic flux that is produced by the magnet 18 for one motor pole of the motor 10. In particular, η represents a ratio of the leakage magnetic flux of the magnetic flux that flows through the leakage magnetic flux path 46 relative to the total magnetic flux of the magnetic flux that is produced by the magnet 18 while the stator 14 is unloaded (i.e., while the magnetomotive force of the stator windings 34 is zero).

In the illustrated embodiment, the expression (1) represents the relationship between the magnetic resistance of the first and second main magnetic flux paths 40 and 42 and the leakage magnetic flux path 46, the magnetomotive force of the magnets 18, and the magnetomotive force of the stator 14 under the loaded condition of the stator 14 in which load current is applied to the stator 14. On the other hand, the expression (2) represents the relationship under the no-load condition in which load current is not applied to the stator 14.

With the motor 10 configured as above, the motor 10 has the flux barrier 24 serving as a magnetic barrier on the magnetic flux path of the magnetic flux induced by the stator 14 between adjacent pair of the magnets 18 such that the magnetic resistance of the leakage magnetic flux path 46 connecting between the different magnetic poles of the same magnet 18 is smaller than the magnetic resistance of the magnetic flux path connecting between different magnetic poles of the adjacent pair of the magnets 18. The motor 10 also has the side opening 26 about the end portion of the magnet 18. With this configuration, the motor 10 can achieve a motor property in which the flux linkage is maximized at the same level as that of the conventional motors under maximum loaded condition while keeping the flux linkage lower than that of conventional motors under low-loaded condition or no-load condition by configuring the motor 10 to satisfy the conditions expressed by the expressions (1) and (2).

In particular, in the illustrated embodiment, with the motor 10, more than 20% of the total magnetic flux of the magnetic flux that is produced by the magnets 18 leaks via the leakage magnetic flux paths 46 on the leakage sections 22 under the no-load condition. Furthermore, due to the flux barrier 24 and the side opening 26, the magnetic flux induced by the stator 14 mainly flows through the leakage magnetic flux paths 46, thereby canceling the leakage magnetic flux on the leakage magnetic flux paths 46 under the loaded condition. In particular, the leakage magnetic flux paths 46 are located near the flux barriers 24 to cross-couple with the q-axis, which cancels the leakage magnetic flux on the leakage magnetic flux paths 46 under the loaded condition. As a result, with the motor 10, high variable flux property in the amount of the flux linkage can be expected. For example, loss reduction by more than 20% can be expected at a high speed and low torque operation without eliminating torque capability. Also, maximum flux linkage can be obtained under the maximum loaded condition.

Also, the leakage sections 22 can serve as a reinforcement member that receives the centrifugal force exerted on the magnets 18 during rotation of the rotor 12. In the illustrated embodiment, the width of the leakage sections 22 naturally becomes larger. As a result, the motor 10 can be driven in a higher speed than the conventional motor, or the motor 10 can have a larger diameter than the conventional motor without deteriorating the motor output property.

Accordingly, with this configuration, the motor 10 can have a magnetic flux property that interlinks with the stator 14 such that the magnetic flux property changes according to the magnetic flux induced by the stator 14 without changing the magnetization level of the permanent magnet as in the conventional motor. Also, with the motor 10, the increase of the copper loss can be suppressed and thus the motor efficiency in high speed and low torque operation can be improved. Also, since the same maximum magnetic flux linkage can be obtained at full load, the maximum motor output torque property can be maintained without any increase in the size of the motor.

In the illustrated embodiment, with the motor 10 in accordance with one aspect, the rotor 12, the stator 14, and the magnets 18 are configured to satisfy the expressions (1) and (2).

With this configuration, the flux linkage in the stator 14 due to the magnets 18 increases as the magnetic flux induced by the stator 14 increases. Thus, the flux linkage in the stator 14 is maximized at the maximum loaded condition. Furthermore, with this configuration, the rigidity of the rotor 12 is increased relative to a conventional rotor. Thus, the motor 10 can be provided with a rotor with a larger diameter, or can bear a higher speed operation. Accordingly, with this configuration, the increase of the copper loss can be suppressed and the iron loss in a high speed and low torque operation can be decreased while maintaining a maximum output, which improves the motor efficiency. Also, high variable flux property can be obtained by leaking the magnetic flux via the leakage magnetic flux path 46 that is highly cross-coupled with the q-axis.

In the illustrated embodiment, with the motor 10 in accordance with one aspect, the leakage magnetic flux path 46 extends between different magnetic poles of the same magnet piece 18a or 18b. In particular, the motor 10 has the leakage magnetic flux path 46 between opposite sides of the same magnet piece 18a or 18b.

With this configuration, the flux linkage can be changed according to the change in the magnetic flux induced by the stator 14 by merely providing a small leakage section 22 about the end portion of the magnet piece 18a or 18b. Thus, with this configuration, the motor efficiency can be improved while suppressing the increase in the size of the motor 10. Also, higher variable flux property can be obtained by highly cross-coupling the leakage magnetic flux path 46 with the q-axis.

In the illustrated embodiment, with the motor 10 in accordance with one aspect, the magnetic resistance calculated based on the magnetic path width and the magnetic path length of the leakage section 22 along the leakage magnetic flux path 46 is smaller than the magnetic resistance of the magnetic path extending between different magnetic poles of the adjacent pair of the magnets 18 (e.g., the magnet piece 18a and the adjacent magnet piece 18b that is adjacent to the magnet piece 18a).

With this configuration, the magnetic flux induced by the stator 14 and the leakage magnetic flux can be cross-coupled, and the change amount in the flux linkage due to increase of the load current in the stator 14 can be made larger. Thus, the iron loss in a high speed and low torque operation can be decreased, which improves the motor efficiency.

In the illustrated embodiment, with the motor 10 in accordance with one aspect, the rotor core 16 has the flux barrier 24 (e.g., the magnetic barrier) disposed between the adjacent pair of the magnets 18 (e.g., the magnet piece 18a and the adjacent magnet piece 18b that is adjacent to the magnet piece 18a), and the side opening 26 circumferentially adjacent to the end portion of the magnet piece 18a or 18b. The leakage magnetic flux path 46 extends on the rotor core 16 between the flux barrier 24 and the side opening 26.

With this configuration, the magnetic flux induced by the stator 14 and the leakage magnetic flux can be well cross-coupled, and the change amount in the flux linkage due to increase of the load current in the stator 14 can be made larger. Thus, the iron loss in a high speed and low torque operation can be decreased, which improves the motor efficiency.

Second Embodiment

Figure 2:
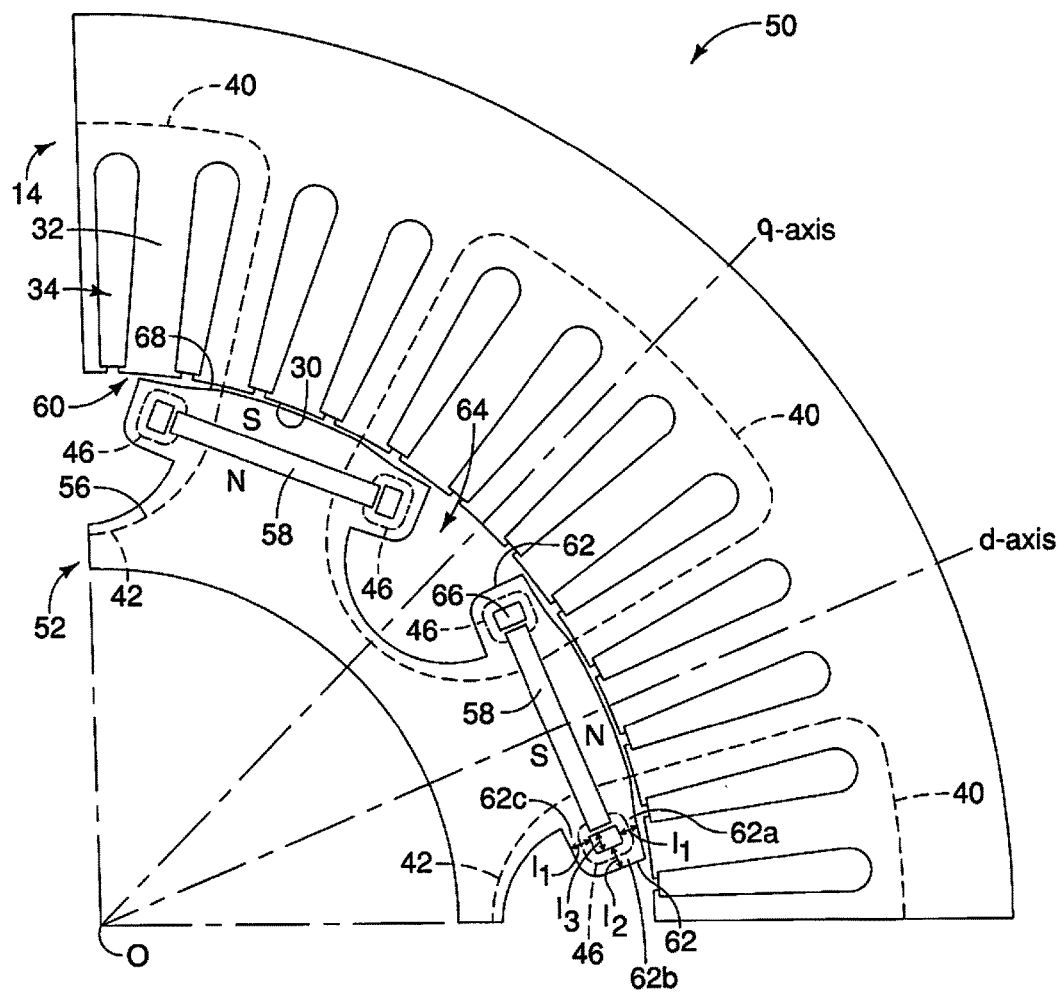
FIG. 2 is a partial cross-sectional schematic view of a permanent magnet synchronous motor in accordance with a second embodiment.

Referring now to FIG. 2, a permanent magnet synchronous motor 50, which can also be referred to as an interior permanent magnet motor, is illustrated in accordance with a second embodiment will now be explained. In view of the similarity between the first and second embodiments, the parts of the second embodiment that are identical to or substantially identical to the parts of the first embodiment will be given the same reference numerals as the parts of the first embodiment. Moreover, the descriptions of the parts of the second embodiment that are identical to the parts of the first embodiment may be omitted for the sake of brevity. Specifically, the motor 50 can be identical to or substantially identical to the motor 10 in accordance with the first embodiment, except for the configuration of a rotor 52. Thus, detail description of the stator 14 will be omitted for the sake of brevity.

As shown in FIG. 2, the rotor 52 has a rotor core 56. The motor 50 also includes a plurality of magnets 58 that is fixedly mounted to the rotor core 56. The rotor core 56 is rotatable relative to the stator 14 about a center rotational axis O of the motor 50, and is radially inwardly disposed relative to the stator 14 with an air gap 60 therebetween. The rotor core 56 is configured to include a plurality pairs of leakage sections 62, a plurality of flux barriers 64 and a plurality pairs of side openings 66. The rotor core 56 is basically formed as a one-piece, unitary member. The configurations of the rotor core 56 will be further described in detail below.

In the illustrated embodiment, the stator 14 is concentrically arranged relative to the rotor 52 with respect to the center rotational axis O of the motor 50. As mentioned above, the stator 14 is radially outwardly disposed relative to the rotor 52 with the air gap 60 therebetween. In particular, as illustrated in FIG. 2, the air gap 60 is present between an outer circumference 68 of the rotor 52 and an inner circumference 30 of the stator 14 to enable the rotor 52 to rotate unrestrictedly or substantially unrestrictedly about the center rotational axis O.

In the illustrated embodiment, the magnets 58 are spaced between adjacent pairs of the flux barriers 64 about the circumference of the rotor 52. As shown in FIG. 2, each of the magnets 58 is formed as a one-piece, unitary member to define each of the motor poles of the motor 50 with alternate polarities. In the illustrated embodiment, eight magnets 58 are alternately arranged in the circumferential direction about the center rotational axis O to define eight motor poles of the motor 50. Specifically, in the illustrated embodiment, the magnets 58 longitudinally extend in a direction perpendicular or substantially perpendicular to a radial direction such that one magnetic pole of the magnets 58 is radially outwardly arranged relative to the other magnetic pole of the magnets 58, for example. Thus, in the illustrated embodiment, the rotor 52 includes eight magnets 58 which are positioned between eight flux barriers 64 and spaced at 45 degree intervals in the circumferential direction about the center rotational axis O. However, the number of the magnets 58 can change with respect to a change in the number of flux barriers 64. Furthermore, each magnet 58 can be configured as a plurality of magnet pieces. As shown in FIG.

2, a d-axis passes through a center of each magnet 58. On the other hand, a q-axis passes through each flux barrier 64. In other words, the q-axis passes between adjacent pair of magnets 58. However, the magnets 58 or the flux barriers 64 can be positioned at any suitable location with respect to the d-axis and the q-axis to achieve the operability of the embodiments discussed herein. Also, the magnets 58 can be arranged in a different manner as needed and/or desired.

In the illustrated embodiment, the magnets 58 form a magnetic structure that produces magnetic fluxes that flow between different magnetic poles of the magnets 58 through a plurality of first main magnetic flux paths 40, a plurality of second main magnetic flux paths 42, and a plurality of leakage magnetic flux paths 46. In the illustrated embodiment, as shown in FIG. 2, each of the first main magnetic flux paths 40 extends from one magnetic pole of one of the magnets 58 to the other magnetic pole of adjacent one of the magnets 58, and passes through the stator winding 34 of the stator 14 via the air gap 60, while each of the second main magnetic flux paths 42 extends from the one magnetic pole of the adjacent one of the magnets 58 to the other magnetic pole of the one of the magnets 58, and passes through the rotor core 56. In the illustrated embodiment, a pair of the first and second main magnetic flux paths 40 and 42 forms a main magnetic flux path that passes through the stator winding 34 of the stator 14 via the air gap 60. On the other hand, the leakage magnetic flux path 46 is located within the rotor core 56 about an end portion of respective one of the magnets 58 near the air gap 60. In the illustrated embodiment, each of the leakage magnetic flux paths 46 extends between different magnetic poles of respective one of the magnets 58 through respective one of the leakage sections 62 of the rotor core 56, respectively.

As mentioned above, the rotor core 56 has the leakage sections 62, the flux barriers 64 and the side openings 66. Although only two pairs of the leakage sections 62 and only two pairs of side openings 66 for two magnets 58 or two motor poles of the motor 50 are shown in FIG. 2, the rotor core 56 has eight pairs of the leakage sections 62 and eight pairs of the side openings 66 corresponding to eight magnets 58 or eight motor poles of the motor 50 in total. Similarly, Although only one full and two partial flux barriers 64 for two magnets 58 or two motor poles of the motor 50 are shown in FIG. 2, the rotor core 56 has eight flux barriers 64 between adjacent pairs of eight magnets 58 or eight motor poles of the motor 50 in total. However, the rotor core 56 can include as many numbers of the leakage sections 62, the flux barriers 64 and the side openings 66 as deemed appropriate for the environment in which the motor 50 is employed. In the illustrated embodiment, the rotor core 56 is configured in a mirror symmetric manner with respect to the d-axis and the q-axis.

As shown in FIG. 2, the leakage sections 62 basically include a squared U-shaped part that extends between different magnetic poles of the magnets 58 to define the leakage magnetic flux paths 46 therewithin, respectively. In other words, in the illustrated embodiment, the leakage magnetic flux paths 46 extend through the leakage sections 62, respectively. More specifically, as shown in FIG. 2, each of the leakage sections 62 mainly includes an outside circumferential portion 62a (e.g., a circumferential portion), a radial portion 62b, and an inside circumferential portion 62c (e.g., a circumferential portion). The outside circumferential portion 62a circumferentially extends away from respective one of the magnets 58. The radial portion 62b radially inwardly extends from the outside circumferential portion 62a. In the illustrated embodiment, the radial portion 62b extends perpendicular to or substantially perpendicular to the outside circumferential portion 62a. The inside circumferential portion 62c is disposed radially inwardly relative to the outside circumferential portion 62a, and circumferentially extends towards the respective one of the magnets 58 from the radial portion 62b. In the illustrated embodiment, the inside circumferential portion 62c extends perpendicular to or substantially perpendicular to the radial portion 62b. With this configuration, the leakage sections 62 define rectangular side openings 66 therewithin, respectively.

In the illustrated embodiment, as shown in FIG. 2, the leakage magnetic flux path 46 extends along the outside circumferential portion 62a, the radial portion 62b, and the inside circumferential portion 62c. Specifically, as shown in FIG. 2, the outside and inside circumferential portions 62a and 62c have a magnetic path width 11 relative to the leakage magnetic flux path 46, while the radial portion 62b has a magnetic path width 12 relative to the leakage magnetic flux path 46 that is smaller than the magnetic path width 11 (11>12). Also, as shown in FIG. 2, the outside and inside circumferential portions 62a and 62c have a magnetic path length 13 along the leakage magnetic flux path 46, which also defines the dimension of one side of the rectangle side opening 66. In the illustrated embodiment, the leakage sections 62 are configured such that the magnetic resistance of the circumferential portion calculated based on the magnetic path width (11) and the magnetic path length (13) of the leakage magnetic flux path 46 along the outside and inside circumferential portions 62a and 62c is smaller than the magnetic resistance of the radial portion 62b calculated based on the magnetic path width (12) and a magnetic path length (between the outside and inside circumferential portions 62a and 62c) of the leakage magnetic flux path 46 along the radial portion 62b. In particular, in the illustrated embodiment, the leakage sections 62 are configured such that the magnetic resistance of the outside and inside circumferential portions 62a and 62c calculated with the ratio of the magnetic path length (13) and magnetic path width (11) is smaller than the magnetic resistance of the radial portion 62b calculated with the ratio of the magnetic path length (between the outside and inside circumferential portions 62a and 62c) and the magnetic path width (12). In particular, in the illustrated embodiment, the leakage sections 62 are configured such that the total magnetic resistance of the outside and inside circumferential portions 62a and 62c is smaller than the magnetic resistance of the radial portion 62b. However, the leakage sections 62 can also be configured such that at least one of the magnetic resistance of the outside circumferential portion 62a and the magnetic resistance of the inside circumferential portion 62c is smaller than the magnetic resistance of the radial portion 62b.

As shown in FIG. 2, the leakage sections 62 for adjacent pairs of the magnets 58 circumferentially face with each other via the flux barriers 64, respectively. In other words, the flux barriers 64 are disposed between adjacent pairs of the leakage sections 62. Specifically, the flux barriers 64 are disposed between the adjacent pairs of the magnets 58 or the adjacent pairs of the motor poles of the motor 50. In the illustrated embodiment, the flux barriers 64 are configured as air gaps between the adjacent pairs of the leakage sections 62. Thus, the magnetic resistance calculated based on a magnetic path width and a magnetic path length of the leakage magnetic flux path 46 on the leakage section 62 is smaller than the magnetic resistance of a magnetic path extending between different magnetic poles of the adjacent pair of the magnets 58 through the flux barriers 64. In the illustrated embodiment, the flux barriers 64 are radially outwardly open to face with the inner circumference 30 of the stator 14, and radially extend from the outer circumference 68 of the rotor 52 to a position radially inward relative to a radially inward boundary of the magnets 58 or the leakage sections 62. In the illustrated embodiment, the flux barriers 64 are configured as air gaps. However, the flux barriers 64 can also include any suitable type of insulating material as is conventional in the art. The side openings 66 are circumferentially adjacent to the end portions of the magnets 58 such that the leakage sections 62 are disposed between the flux barriers 64 and the side openings 66, respectively. Thus, the leakage magnetic flux paths 46 that extend through the leakage sections 62 extend on the rotor core 56 between the flux barriers 64 and the side openings 66, respectively.

In the illustrated embodiment, the rotor 52, the stator 14, and the magnets 58 (e.g., the magnetic structure) are further configured to satisfy the following expressions (1) and (2) for one motor pole of the motor 50.

$$Vs \geq \frac{Rg + Rs}{Rr} Vm \quad (1)$$

$$\eta = \frac{Rg + Rs}{Rb + Rg + Rs} \geq 0.2 \quad (2)$$

Here, Vs represents the magnetomotive force of the stator windings 34 for one motor pole of the motor 50, and Vm represents the magnetomotive force of the magnet 58 for one motor pole of the motor 50. Rg represents the magnetic resistance of the air gap 60 for one motor pole of the motor 50, Rs represents the magnetic resistance of the stator 14 along the first main magnetic flux path 40 for one motor pole of the motor 50, Rr represents the magnetic resistance of the rotor core 56 along the second main magnetic flux path 42 for one motor pole of the motor 50, Rb represents the magnetic resistance of the rotor core 56 along the leakage magnetic flux path 46, and η represents a ratio of a leakage magnetic flux of the magnetic flux that flows through the leakage magnetic flux path 46 relative to a total magnetic flux of the magnetic flux that is produced by the magnet 58 for one motor pole of the motor 50. In particular, η represents a ratio of the leakage magnetic flux of the magnetic flux that flows through the leakage magnetic flux path 46 relative to the total magnetic flux of the magnetic flux that is produced by the magnet 58 while the stator 14 is unloaded (i.e., while the magnetomotive force of the stator windings 34 is zero).

In the illustrated embodiment, the expression (1) represents the relationship between the magnetic resistance of the first and second main magnetic flux paths 40 and 42 and the leakage magnetic flux path 46, the magnetomotive force of the magnets 58, and the magnetomotive force of the stator 14 under the loaded condition of the stator 14 in which load current is applied to the stator 14. On the other hand, the expression (2) represents the relationship under the no-load condition in which load current is not applied to the stator 14.

With the motor 50 configured as above, the motor 50 basically has the same advantages as the motor 10 in accordance with the first embodiment. Furthermore, in the illustrated embodiment, each of the leakage sections 62 has the outside and inside circumferential portions 62a and 62c and the radial portion 62b, and the leakage magnetic flux path 46 extends along the outside circumferential portion 62a, the radial portion 62b, and the inside circumferential portion 62c. Also, the magnetic resistance of the outside and inside circumferential portions 62a and 62c along the leakage magnetic flux path 46 is smaller than the magnetic resistance of the radial portion 62b along the leakage magnetic flux path 46. Thus, the motor 50 can achieve a motor property in which the flux linkage is maximized at the same level as that of the conventional motors under maximum load condition while keeping the flux linkage lower than that of conventional motors under low-loaded condition or no-load condition. Furthermore, the instantaneous change in the saliency ratio accompanied by the increase in the magnetic flux induced by the stator 14 can be suppressed. The saliency ratio is defined by the ratio of the inductance in the d-axis direction and the inductance in the q-axis. Generally, with the saliency-based rotor position sensing method, the variation of the saliency largely affects the detection accuracy. However, with the motor 50, the detection accuracy can be largely improved. As a result, with this configuration, the manufacturing cost can be lowered by eliminating the rotor position sensor while improving the motor efficiency.

In the illustrated embodiment, with the motor 50 in accordance with one aspect, the rotor core 56 has the outside and inside circumferential portions 62a and 62c circumferentially extending and the radial portion 62b radially extending between the outside and inside circumferential portions 62a and 62c. The leakage magnetic flux path 46 extends along the outside circumferential portion 62a, the radial portion 62b, and the inside circumferential portion 62c of the rotor core 56. The magnetic resistance of the outside and inside circumferential portions 62a and 62c calculated based on the magnetic path width 11 and the magnetic path length 13 of the leakage magnetic flux path 46 along the outside and inside circumferential portions 62a and 62c is smaller than the magnetic resistance of the radial portion 62b calculated based on the magnetic path width 12 and the magnetic path length of the leakage magnetic flux path 46 along the radial portion 62b.

With this configuration, the deterioration of the rotor position sensing property due to increase of the magnetic flux induced by the stator 14 can be suppressed. Thus, the manufacturing cost can be lowered by eliminating the rotor position sensor while improving the motor efficiency.

Also, with the motor 50, the leakage magnet flux path 46 has a rectangular shape about the end portion of the magnet 58 along the leakage section 62, which balances variable flux linkage and the self-sensing property. Furthermore, with the motor 50, the magnetic path width 11 of the outside and inside circumferential portions 62a and 62c is larger than the magnetic path width 12 of the radial portion 62b, which also improves the self-sensing property.

Third Embodiment

Figure 3:
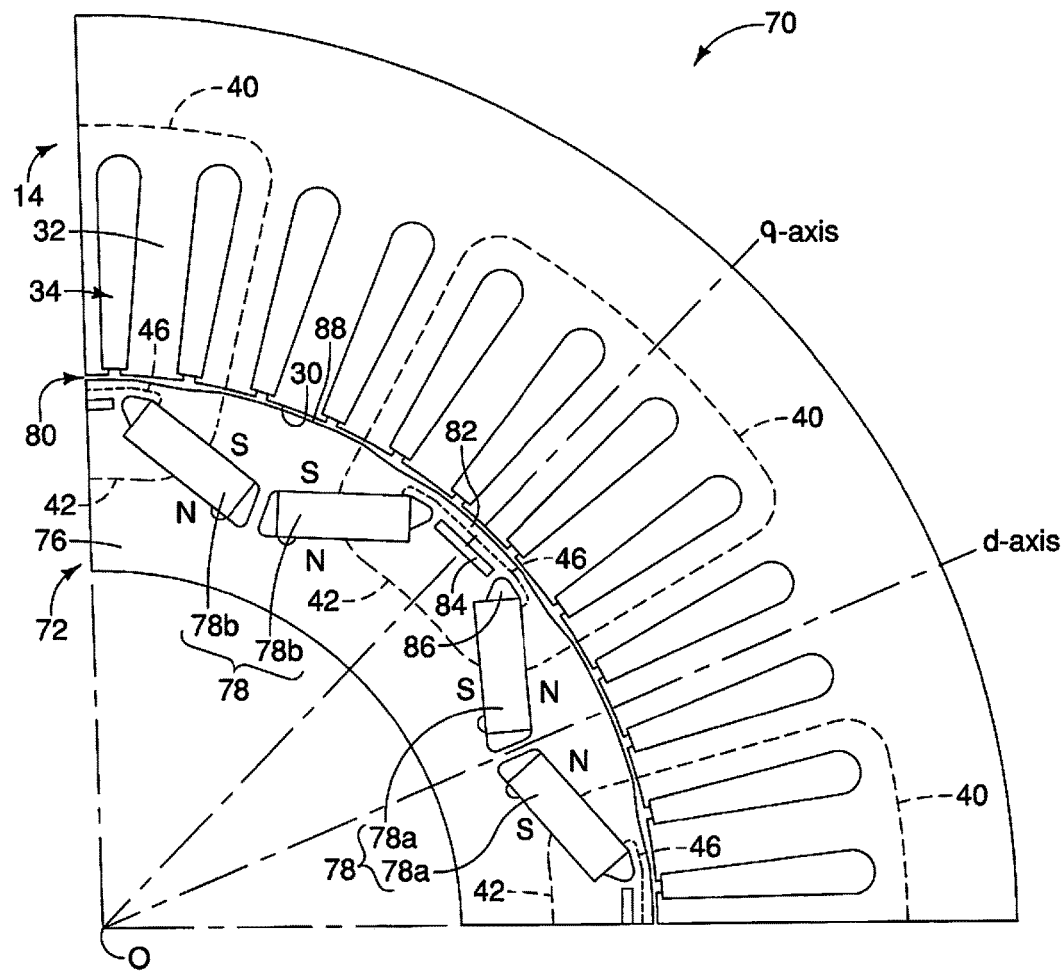
FIG. 3 is a partial cross-sectional schematic view of a permanent magnet synchronous motor in accordance with a third embodiment.
Figure 4:
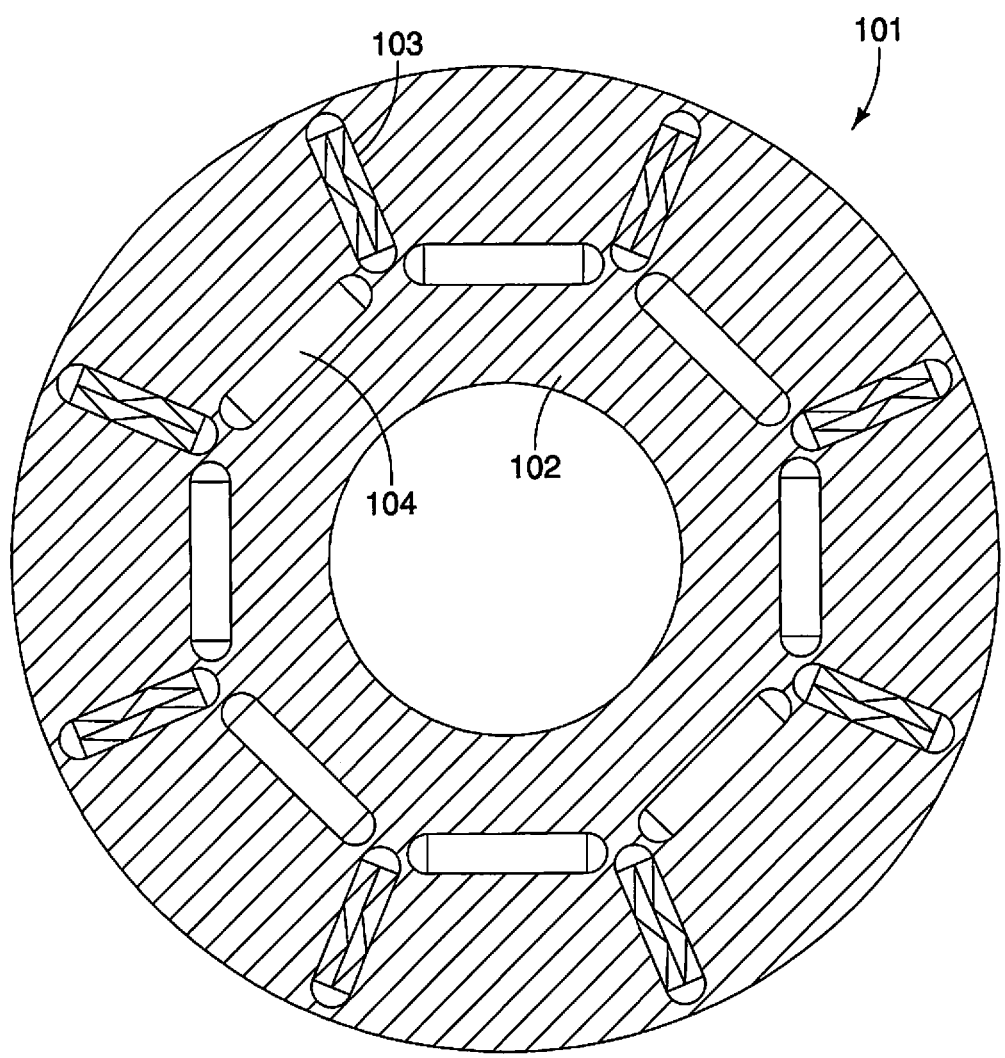
FIG. 4 is a cross-sectional schematic view of a variable magnetization motor.

Referring now to FIG. 3, a permanent magnet synchronous motor 70, which can also be referred to as an interior permanent magnet motor, is illustrated in accordance with a second embodiment will now be explained. In view of the similarity between the first to third embodiments, the parts of the third embodiment that are identical to or substantially identical to the parts of the first and second embodiments will be given the same reference numerals as the parts of the first and second embodiment. Moreover, the descriptions of the parts of the third embodiment that are identical to the parts of the first and second embodiments may be omitted for the sake of brevity. Specifically, the motor 70 can be identical to or substantially identical to the motor 10 in accordance with the first embodiment, except for the configuration of a rotor 72. Thus, detail description of the stator 14 will be omitted for the sake of brevity.

In the illustrated embodiment, the rotor 72 has a rotor core 76. The motor 70 also includes a plurality of magnets 78 that is fixedly mounted to the rotor core 76. The rotor core 76 is rotatable relative to the stator 14 about a center rotational axis O of the motor 70, and is radially inwardly disposed relative to the stator 14 with an air gap 80 therebetween. The rotor core 76 is configured to include a plurality of leakage sections 82, a plurality of flux barriers 84 and a plurality pairs of side openings 86. The rotor core 76 is basically formed as a one-piece, unitary member. The configurations of the rotor core 76 will be further described in detail below.

In the illustrated embodiment, the stator 14 is concentrically arranged relative to the rotor 72 with respect to the center rotational axis O of the motor 70. As mentioned above, the stator 14 is radially outwardly disposed relative to the rotor 72 with the air gap 80 therebetween. In particular, as illustrated in FIG. 3, the air gap 80 is present between an outer circumference 88 of the rotor 72 and an inner circumference 30 of the stator 14 to enable the rotor 72 to rotate unrestrictedly or substantially unrestrictedly about the center rotational axis O.

In the illustrated embodiment, the magnets 78 are spaced between adjacent pairs of the flux barriers 84 about the circumference of the rotor 72. As shown in FIG. 3, each of the magnets 78 has a pair of permanent magnet pieces 78a or 78b (e.g., at least one permanent magnet) to define each of the motor poles of the motor 70 with alternate polarities. In the illustrated embodiment, four pairs of the magnet pieces 78a and four pairs of the magnet pieces 78b are alternately arranged in the circumferential direction about the center rotational axis O to define eight motor poles of the motor 70. Specifically, in the illustrated embodiment, the north poles of the magnet pieces 78a are radially outwardly arranged relative to the south poles of the magnet pieces 78a, while the south poles of the magnet pieces 78b are radially outwardly arranged relative to the north poles of the magnet pieces 78b, for example. Thus, in the illustrated embodiment, the rotor 72 includes eight pairs of the magnet pieces 78a and 78b which are positioned between eight flux barriers 84 and spaced at 45 degree intervals in the circumferential direction about the center rotational axis O. However, the number of the magnet pieces 78a and 78b or the number of the magnets 78 can change with respect to a change in the number of flux barriers 84. Furthermore, each magnet 78 can be configured as a single magnet piece or more than two magnet pieces. As shown in FIG. 3, a d-axis passes through a center of each magnet 78. In other words, the d-axis passes through between the pair of magnet pieces 78a or 78b. On the other hand, a q-axis passes through each flux barriers 84. In other words, the q-axis passes between adjacent pair of magnets 78, or adjacent pair of the magnet pieces 78a and 78b. However, the magnets 78 or the flux barriers 84 can be positioned at any suitable location with respect to the d-axis and the q-axis to achieve the operability of the embodiments discussed herein. In the illustrated embodiment, the pair of the magnet pieces 78a extends radially and inwardly as circumferentially moving towards each other. Similarly, the pair of the magnet pieces 78b extends radially and inwardly as circumferentially moving towards each other. However, the magnet pieces 78a and 78b can be arranged in a different manner as needed and/or desired.

In the illustrated embodiment, the magnets 78 form a magnetic structure that produces magnetic flux that flows between different magnetic poles of the magnets 78 through a plurality of first main magnetic flux paths 40, a plurality of second main magnetic flux paths 42, and a plurality of leakage magnetic flux paths 46. In the illustrated embodiment, as shown in FIG. 3, each of the first main magnetic flux paths 40 extends from one magnetic pole of one of the magnets 78 (e.g., the north pole of the magnet piece 78a) to the other magnetic pole of adjacent one of the magnets 78 (e.g., the south pole of the magnet piece 78b), and passes through the stator winding 34 of the stator 14 via the air gap 80, while each of the second main magnetic flux paths 42 extends from the one magnetic pole of the adjacent one of the magnets 78 (e.g., the north pole of the magnet piece 78b) to the other magnetic pole of the one of the magnets 78 (e.g., the south pole of the magnet piece 78a), and passes through the rotor core 76. In the illustrated embodiment, a pair of the first and second main magnetic flux paths 40 and 42 forms a main magnetic flux path that passes through the stator winding 34 of the stator 14 via the air gap 80. On the other hand, each of the leakage magnetic flux paths 46 is located within the rotor core 76 about an end portion of respective one of the magnet pieces 78a and 78b near the air gap 80. In the illustrated embodiment, each of the leakage magnetic flux paths 46 extends between different magnetic poles of an adjacent pair of the magnets 78 (e.g., between the north pole of the magnet piece 78a and the south pole of the magnet piece 78b) through respective one of the leakage sections 82 of the rotor core 76.

As mentioned above, the rotor core 76 has the leakage sections 82, the flux barriers 84 and the side openings 86. Although only one full and two partial leakage sections 82 and only one full and two partial flux barriers 84 for two magnets 78 or two motor poles of the motor 70 are shown in FIG. 3, the rotor core 76 has eight leakage sections 82 and eight flux barriers 84 corresponding to eight magnets 78 in total. Similarly, only two pairs the side openings 86 for two magnets 78 or two motor poles of the motor 70 are shown in FIG. 3, the rotor core 76 has eight pairs of the side openings 86 corresponding to eight magnets 78 or eight motor poles of the motor 70 in total. However, the rotor core 76 can include as many numbers of the leakage sections 82, the flux barriers 84 and the side openings 86 as deemed appropriate for the environment in which the motor 70 is employed. In the illustrated embodiment, the rotor core 76 is configured in a mirror symmetric manner with respect to the d-axis and the q-axis.

As shown in FIG. 3, the leakage sections 82 basically extend between different magnetic poles of adjacent pairs of the magnets 78, respectively, to define the leakage magnetic flux paths 46 therewithin, respectively. In other words, in the illustrated embodiment, the leakage magnetic flux paths 46 extend through the leakage sections 82, respectively. As shown in FIG. 3, the leakage sections 82 radially face with the inner circumference 30 of the stator 14 via the air gap 80. Specifically, each of the leakage sections 82 is present between the radially outward boundary of respective one of the flux barriers 84 and the outer circumference 88 of the rotor 72. Also, the leakage sections 82 circumferentially extend between adjacent pairs of the magnets 78. Thus, in the illustrated embodiment, the leakage magnetic flux paths 46 extend between different magnetic poles of the adjacent pairs of the magnets 78 (e.g., between the magnet piece 78a and the magnet piece 78b that is adjacent to the magnet piece 78a), respectively. As shown in FIG. 3, the flux barriers 84 are also circumferentially disposed between adjacent pairs of the magnets 78 or between adjacent pairs of the side openings 86. Specifically, the flux barriers 84 are disposed between the adjacent pairs of the magnets 78 or the adjacent pairs of the motor poles of the motor 70 (e.g., between the magnet piece 78a and the magnet piece 78b that is adjacent to the magnet piece 78a). In the illustrated embodiment, the flux barriers 84 are configured as air gaps between the adjacent pairs of the magnets 78 (e.g., between the magnet piece 78a and the magnet piece 78b that is adjacent to the magnet piece 78a) such that the magnetic resistance calculated based on a magnetic path width and a magnetic path length of the leakage magnetic flux path 46 is smaller than the magnetic resistance of a magnetic path extending between different magnetic poles of the same magnets 78 (e.g., between the north pole of the magnet piece 78a and the south pole of the same magnet piece 78a) through the flux barriers 84. In the illustrated embodiment, the flux barriers 84 are configured as air gaps. However, the flux barriers 84 can also include any suitable type of insulating material as is conventional in the art. The side openings 86 are circumferentially adjacent to the end portions of the magnet pieces 78a and 78b.

In the illustrated embodiment, the rotor 72, the stator 14, and the magnets 78 (e.g., the magnetic structure) are further configured to satisfy the following expressions (1) and (2) for one motor pole of the motor 70.

$$Vs \geq \frac{Rg + Rs}{Rr} Vm \quad (1)$$

$$\eta = \frac{Rg + Rs}{Rb + Rg + Rs} \geq 0.2 \quad (2)$$

Here, Vs represents the magnetomotive force of the stator windings 34 for one motor pole of the motor 70, and Vm represents the magnetomotive force of the magnet 78 for one motor pole of the motor 70. Rg represents the magnetic resistance of the air gap 80 for one motor pole of the motor 70, Rs represents the magnetic resistance of the stator 14 along the first main magnetic flux path 40 for one motor pole of the motor 70, Rr represents the magnetic resistance of the rotor core 76 along the second main magnetic flux path 42 for one motor pole of the motor 70, Rb represents the magnetic resistance of the rotor core 76 along the leakage magnetic flux path 46, and η represents a ratio of a leakage magnetic flux of the magnetic flux that flows through the leakage magnetic flux path 46 relative to a total magnetic flux of the magnetic flux that is produced by the magnet 78 for one motor pole of the motor 70. In particular, η represents a ratio of the leakage magnetic flux of the magnetic flux that flows through the leakage magnetic flux path 46 relative to the total magnetic flux of the magnetic flux that is produced by the magnet 78 while the stator 14 is unloaded (i.e., while the magnetomotive force of the stator windings 34 is zero).

In the illustrated embodiment, the expression (1) represents the relationship between the magnetic resistance of the first and second main magnetic flux paths 40 and 42 and the leakage magnetic flux path 46, the magnetomotive force of the magnets 78, and the magnetomotive force of the stator 14 under the loaded condition of the stator 14 in which load current is applied to the stator 14. On the other hand, the expression (2) represents the relationship under the no-load condition in which load current is not applied to the stator 14.

With the motor 70 configured as above, the motor 70 basically has the same advantages as the motor 10 in accordance with the first embodiment. Furthermore, in the illustrated embodiment, as shown in FIG. 3, the motor 70 has the leakage magnetic flux paths 46 extending between different magnetic poles of the adjacent pairs of the magnets 78 (e.g., between the north pole of the magnet piece 78a and the south pole of the magnet piece 78b that is adjacent to the magnet piece 78a), and the motor 70 is configured to satisfy the conditions expressed by the expressions (1) and (2).

As shown in FIG. 3, the motor 70 has the flux barriers 84 as a magnetic barrier between different magnetic poles of the same magnets 78 (e.g., the magnet piece 78a or 78b) such that the magnetic resistance of the leakage magnetic flux path 46 extending between different magnetic poles of the adjacent pair of the magnets 78 (e.g., between different magnetic poles of the magnet piece 78a and the magnet piece 78b) is smaller than the magnetic resistance of the magnetic flux path extending between different magnetic poles of the same magnet 78. With this configuration, a large magnetic barrier does not need to be provided on the magnetic flux path of the magnetic flux induced by the stator 14. Thus, the saliency ratio can be made larger, which can increase the reluctance torque and maintain high power factor of the motor under the load condition. Thus, with this configuration, the increase of the copper loss can be suppressed and thus the motor efficiency in the high speed and low torque operation can be improved. Also, since the same maximum magnetic flux linkage can be obtained at full load, the maximum motor output torque property can be maintained without any increase in the size of the motor.

In the illustrated embodiment, with the motor 70 in accordance with one aspect, the leakage magnetic flux path 46 extends between different magnetic poles of the adjacent pair of the magnets 78.

With this configuration, the flux linkage can be changed according to the change in the magnetic flux induced by the stator 14 by merely providing a small leakage section 82 near the air gap 80. Thus, with this configuration, the motor efficiency can be improved while suppressing the increase in the size of the motor. Also, with this configuration, high q-axis inductance can be maintained to obtain high power factor operation.

In the illustrated embodiment, with the motor 70 in accordance with one aspect, the rotor core 76 has the magnetic barrier 84 that extends between the adjacent pair of the magnets 78 such that the magnetic resistance calculated based on a magnetic path width and a magnetic path length of the leakage magnetic flux path 46 is smaller than the magnetic resistance of a magnetic path extending between different magnetic poles of the same magnet 78.

With this configuration, a large magnetic barrier does not need to be provided on the magnetic flux path of the magnetic flux induced by the stator 14, and the reluctance torque can be increased. Thus, the power factor of the motor under the load condition, and the motor efficiency can be improved while suppressing the drop of the motor output.

Also, with the motor 70, the due to higher inductance in the q-axis direction, higher power factor can be obtained while keeping the same torque compared to a self-leakage type structure.

General Interpretation of Terms

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. The terms of degree such as "substantially", "about" and "approximately" as used herein mean a reasonable amount of deviation of the modified term such that the end result is not significantly changed.

While only selected embodiments have been chosen to illustrate the present invention, it will be apparent to those skilled in the art from this disclosure that various changes and modifications can be made herein without departing from the scope of the invention as defined in the appended claims. For example, the size, shape, location or orientation of the various components can be changed as needed and/or desired. Components that are shown directly connected or contacting each other can have intermediate structures disposed between them. The functions of one element can be performed by two, and vice versa. The structures and functions of one embodiment can be adopted in another embodiment. It is not necessary for all advantages to be present in a particular embodiment at the same time. Every feature which is unique from the prior art, alone or in combination with other features, also should be considered a separate description of further inventions by the applicant, including the structural and/or functional concepts embodied by such features. Thus, the foregoing descriptions of the embodiments according to the present invention are provided for illustration only, and not for the purpose of limiting the invention as defined by the appended claims and their equivalents.

What is claimed is:

1. A permanent magnet synchronous motor comprising:
a stator with a stator winding;
a rotor with a rotor core rotatable relative to the stator, the rotor being radially inwardly or outwardly disposed relative to the stator with an air gap therebetween; and
a magnetic structure with at least one permanent magnet mounted to the rotor core, the magnetic structure producing a magnetic flux that flows between different magnetic poles of the magnetic structure through a main magnetic flux path that passes through the stator winding of the stator via the air gap and a leakage magnetic flux path that is located within the rotor core about an end portion of the permanent magnet near the air gap,
the stator, the rotor and the magnetic structure being further configured to satisfy the following expressions while changing a magnetization state of the permanent magnet of the permanent magnet synchronous motor:

$$Vs \geq \frac{Rg + Rs}{Rr} Vm$$

$$\eta = \frac{Rg + Rs}{Rb + Rg + Rs} \geq 0.2$$

where Vs represents magnetomotive force of the stator winding, Vm represents magnetomotive force of the magnetic structure, Rg represents magnetic resistance of the air gap, Rs represents magnetic resistance of the stator along the main magnetic flux path, Rr represents magnetic resistance of the rotor core along the main magnetic flux path, Rb represents magnetic resistance of the rotor core along the leakage magnetic flux path, and η represents a ratio of a leakage magnetic flux of the magnetic flux that flows through the leakage magnetic flux path relative to a total magnetic flux of the magnetic flux that is produced by the magnetic structure.

2. The permanent magnet synchronous motor according to claim 1, wherein
the leakage magnetic flux path extends between different magnetic poles of the permanent magnet.

3. The permanent magnet synchronous motor according to claim 2, wherein
the rotor core has a magnetic barrier disposed between the permanent magnet and an adjacent permanent magnet that is adjacent to the permanent magnet, and a side opening circumferentially adjacent to the end portion of the permanent magnet, and
the leakage magnetic flux path extends on the rotor core between the magnetic barrier and the side opening.

4. A permanent magnet synchronous motor comprising:
a stator with a stator winding;
a rotor with a rotor core rotatable relative to the stator, the rotor being radially inwardly or outwardly disposed relative to the stator with an air gap therebetween; and
a magnetic structure with at least one permanent magnet mounted to the rotor core, the magnetic structure producing a magnetic flux that flows between different magnetic poles of the magnetic structure through a main magnetic flux path that passes through the stator winding of the stator via the air gap and a leakage magnetic flux path that is located within the rotor core about an end portion of the permanent magnet near the air gap,
the stator, the rotor and the magnetic structure being further configured to satisfy the following expressions:

$$Vs \geq \frac{Rg + Rs}{Rr} Vm$$

$$\eta = \frac{Rg + Rs}{Rb + Rg + Rs} \geq 0.2$$

where Vs represents magnetomotive force of the stator winding, Vm represents magnetomotive force of the magnetic structure, Rg represents magnetic resistance of the air gap, Rs represents magnetic resistance of the stator along the main magnetic flux path, Rr represents magnetic resistance of the rotor core along the main magnetic flux path, Rb represents magnetic resistance of the rotor core along the leakage magnetic flux path, and η represents a ratio of a leakage magnetic flux of the magnetic flux that flows through the leakage magnetic flux path relative to a total magnetic flux of the magnetic flux that is produced by the magnetic structure,
the leakage magnetic flux path extending between different magnetic poles of the permanent magnet,
the rotor core having a circumferential portion circumferentially extending and a radial portion radially extending from the circumferential portion,
the leakage magnetic flux path extending along the circumferential portion and the radial portion of the rotor core, and
the magnetic resistance of the circumferential portion calculated based on a magnetic path width and a magnetic path length of the leakage magnetic flux path along the circumferential portion being smaller than the magnetic resistance of the radial portion calculated based on a magnetic path width and a magnetic path length of the leakage magnetic flux path along the radial portion.

5. The permanent magnet synchronous motor according to claim 1, wherein
the leakage magnetic flux path extends between different magnetic poles of the permanent magnet and an adjacent permanent magnet that is adjacent to the permanent magnet.

6. A permanent magnet synchronous motor comprising:
a stator with a stator winding;
a rotor with a rotor core rotatable relative to the stator, the rotor being radially inwardly or outwardly disposed relative to the stator with an air gap therebetween; and
a magnetic structure with at least one permanent magnet mounted to the rotor core, the magnetic structure producing a magnetic flux that flows between different magnetic poles of the magnetic structure through a main magnetic flux path that passes through the stator winding of the stator via the air gap and a leakage magnetic flux path that is located within the rotor core about an end portion of the permanent magnet near the air gap,
the stator, the rotor and the magnetic structure being further configured to satisfy the following expressions:

$$Vs \geq \frac{Rg + Rs}{Rr} Vm$$

$$\eta = \frac{Rg + Rs}{Rb + Rg + Rs} \geq 0.2$$

where Vs represents magnetomotive force of the stator winding, Vm represents magnetomotive force of the magnetic structure, Rg represents magnetic resistance of the air gap, Rs represents magnetic resistance of the stator along the main magnetic flux path, Rr represents magnetic resistance of the rotor core along the main magnetic flux path, Rb represents magnetic resistance of the rotor core along the leakage magnetic flux path, and η represents a ratio of a leakage magnetic flux of the magnetic flux that flows through the leakage magnetic flux path relative to a total magnetic flux of the magnetic flux that is produced by the magnetic structure,
the leakage magnetic flux path extending between different magnetic poles of the permanent magnet and an adjacent permanent magnet that is adjacent to the permanent magnet, and
the rotor core having a magnetic barrier that extends between the permanent magnet and the adjacent permanent magnet such that the magnetic resistance calculated based on a magnetic path width and a magnetic path length of the leakage magnetic flux path is smaller than the magnetic resistance of a magnetic path extending between different magnetic poles of the permanent magnet.

7. A permanent magnet synchronous motor comprising:
a stator with a stator winding;
a rotor with a rotor core rotatable relative to the stator, the rotor being radially inwardly or outwardly disposed relative to the stator with an air gap therebetween; and
a magnetic structure with at least one permanent magnet mounted to the rotor core, the magnetic structure producing a magnetic flux that flows between different magnetic poles of the magnetic structure through a main magnetic flux path that passes through the stator winding of the stator via the air gap and a leakage magnetic flux path that is located within the rotor core about an end portion of the permanent magnet near the air gap,
the stator, the rotor and the magnetic structure being further configured to satisfy the following expressions:

$$Vs \geq \frac{Rg + Rs}{Rr} Vm$$

$$\eta = \frac{Rg + Rs}{Rb + Rg + Rs} \geq 0.2$$

where Vs represents magnetomotive force of the stator winding, Vm represents magnetomotive force of the magnetic structure, Rg represents magnetic resistance of the air gap, Rs represents magnetic resistance of the stator along the main magnetic flux path, Rr represents magnetic resistance of the rotor core along the main magnetic flux path, Rb represents magnetic resistance of the rotor core along the leakage magnetic flux path, and η represents a ratio of a leakage magnetic flux of the magnetic flux that flows through the leakage magnetic flux path relative to a total magnetic flux of the magnetic flux that is produced by the magnetic structure,
the leakage magnetic flux path extending between different magnetic poles of the permanent magnet, and
the magnetic resistance calculated based on a magnetic path width and a magnetic path length of the leakage magnetic flux path being smaller than the magnetic resistance of a magnetic path extending between different magnetic poles of the permanent magnet and an adjacent permanent magnet that is adjacent to the permanent magnet.

8. The permanent magnet synchronous motor according to claim 7, wherein
the rotor core has a magnetic barrier disposed between the permanent magnet and an adjacent permanent magnet that is adjacent to the permanent magnet, and a side opening circumferentially adjacent to the end portion of the permanent magnet, and
the leakage magnetic flux path extends on the rotor core between the magnetic barrier and the side opening.

9. The permanent magnet synchronous motor according to claim 7, wherein
the rotor core has a circumferential portion circumferentially extending and a radial portion radially extending from the circumferential portion,
the leakage magnetic flux path extends along the circumferential portion and the radial portion of the rotor core, and
the magnetic resistance of the circumferential portion calculated based on a magnetic path width and a magnetic path length of the leakage magnetic flux path along the circumferential portion is smaller than the magnetic resistance of the radial portion calculated based on a magnetic path width and a magnetic path length of the leakage magnetic flux path along the radial portion.

* * * * *